(12) United States Patent
Hataoka

(10) Patent No.: US 7,566,572 B2
(45) Date of Patent: Jul. 28, 2009

(54) IMMUNOLOGICAL ASSAY AND CHIP

(75) Inventor: Yukari Hataoka, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 11/896,014

(22) Filed: Aug. 29, 2007

(65) Prior Publication Data

US 2008/0138831 A1    Jun. 12, 2008

Related U.S. Application Data

(63) Continuation of application No. PCT/JP2007/055648, filed on Mar. 20, 2007.

(30) Foreign Application Priority Data

Apr. 25, 2006    (JP) .............................. 2006-120917

(51) Int. Cl.
    *G01N 33/558*    (2006.01)
(52) U.S. Cl. .................................................... 436/514
(58) Field of Classification Search .................. None
    See application file for complete search history.

(56) References Cited

U.S. PATENT DOCUMENTS

| 5,458,852 | A * | 10/1995 | Buechler ..................... 422/58 |
| 6,436,722 | B1 * | 8/2002 | Clark et al. ................. 436/518 |
| 2003/0180814 | A1 | 9/2003 | Hodges et al. |
| 2004/0115838 | A1 * | 6/2004 | Quake et al. ................ 436/538 |

FOREIGN PATENT DOCUMENTS

| JP | 2-62952 | 3/1990 |
| JP | 2001-296298 A | 10/2001 |
| JP | 2007-64827 A | 3/2007 |
| WO | WO 2007/026731 A1 | 3/2007 |

OTHER PUBLICATIONS

Barker, et al., "Control of Flow Direction in Microfluidic Devices with Polyelectrolyte Multilayers," National Institute of Standards & Technology, Analytical Chemistry, vol. 72, No. 24, Dec. 15, 2000.
Hisamoto, et al., "On-Chip Integration of Sequential Ion-Sensing System Based on Intermittent Reagent Pumping and Formation of Two-Layer Flow," Department of Applied Chemistry, Graduate School of Engineering, The University of Tokyo, Analytical Chemistry, vol. 73, No. 22, Nov. 15, 2001.
Duffy, et al., "Microfabricated Centrifugal Microfluidic Systems: Characterization and Multiple Enzymatic Assays," Gamera Biosicence, Analytical Chemistry, vol. 71, No. 20, Oct. 15, 1999.

* cited by examiner

*Primary Examiner*—Ann Y Lam
(74) *Attorney, Agent, or Firm*—McDermott Will & Emery LLP

(57) ABSTRACT

The present invention provides an immunological assay suitable to be carried out on a chip. After an antigen-antibody complex in which an antigen to be measured and an antibody have bound to each other was obtained in a reaction chamber, the reaction chamber is washed using a sample solution and thereby the antigen-antibody complex and the antibody that has not bound to the antigen to be measured are separated from each other. According to the present invention, the reaction chamber can be washed to an extent that allows a signal reflecting the amount of the antigen to be measured to be detected with accuracy comparable to the case of using a wash solution without using a wash solution that is typified by Tris-HCl buffer that does not contain any antigens to be measured such as protein. Thus, it is not necessary to supply a wash solution from the outside of the chip or to allow a wash solution to be retained on the chip beforehand. Accordingly, an immunological assay can be carried out easily on a chip.

6 Claims, 6 Drawing Sheets

(1-A)

(1-B)

(1-C)

Measurement (5-A)

(5-B)

(5-C)

(5-D)

(5-E)

Measurement

IMMUNOLOGICAL ASSAY AND CHIP

This Application is a continuation of International Application No. PCT/JP2007/055648, whose international filing date is Mar. 20, 2007 which in turn claims the benefit of Japanese Patent Application No. 2006-120917, filed on Apr. 25, 2006, the disclosures of which Applications are incorporated by reference herein. The benefit of the filing and priority dates of the International and Japanese Applications is respectfully requested.

TECHNICAL FIELD

The present invention relates to an immunological assay for measuring the amount of a specific component in a sample solution by using an antigen-antibody reaction, particularly an immunological assay suitable to be carried out on a chip. Furthermore, the present invention also relates to a chip suitable for carrying out the immunological assay.

BACKGROUND ART

Immunological assays are receiving attention as a method of identifying and quantitating, with high accuracy, proteins such as virus, bacteria, and allergenic substance contained in biological samples (for example, blood).

The immunological assay is roughly classified into an immunonephelometry and an immunolabeling assay. The immunonephelometry is a method of determining the change in turbidity of a sample solution that is caused by an antigen-antibody complex produced by an antigen-antibody reaction. The immunolabeling assay is a method of determining the change in the amount of a labeling substance after an antigen-antibody reaction by using an antibody labeled with the labeling substance.

The immunolabeling assay is subdivided according to the type of the labeling substance. Examples thereof include a radioimmunoassay in which a radioisotope is used as the labeling substance, an enzyme immunoassay (EIA) in which an enzyme is used, and a fluorescence immunoassay in which a fluorescent substance is used. In the EIA, as compared to other immunolabeling assays, the safety of the labeling substance is higher, it can be carried out by a simpler operation, and the measurement accuracy is higher. Therefore the EIA is used frequently.

A typical example of the EIA is an enzyme-linked immunosorbent assay (ELISA). An example of the ELISA is described with reference to FIG. 1.

<Step 1-A: Forming a Solid-Phase Antigen>

A solution containing a capture antigen having an epitope identical to that of an antigen to be measured is introduced into a reaction chamber 7 and is maintained at a predetermined temperature for a predetermined period of time, and thereby the capture antigen is allowed to adsorb to the surface of the reaction chamber 7. Thereafter the capture antigen to be allowed to adsorb is covered with protein that is not involved in a later antigen-antibody reaction and enzyme reaction (blocking). Thus a solid-phase antigen 6 is formed inside the reaction chamber 7. The solid-phase antigen 6 is being fixed to the surface of the reaction chamber 7 and therefore is not removed from the reaction chamber 7 by the washing described later.

<Step 1-B: Binding Reactions Between Antibody and Antigen to be Measured as Well as Solid-Phase Antigen>

An antibody 3 that specifically binds to an antigen to be measured 2 is added to a sample solution 9. The antibody 3 is being labeled with a labeling substance (for example, an enzyme) 4. Thereafter, the sample solution 9 containing the antibody 3 is introduced into the reaction chamber 7. Thus, the antigen-antibody reaction proceeds between the antibody 3 and the antigen to be measured 2 as well as the solid-phase antigen 6 in the reaction chamber 7.

<Step 1-C: Removal of Unreacted Antibody and Antigen-Antibody Complex>

Using a wash solution 10 typified by Tris-HCl buffer, the inside of the reaction chamber 7 is washed. Thereby the antigen-antibody complex formed through binding of the antibody 3 to the antigen to be measured 2 and the antibody 3 that has not been bound to the solid-phase antigen 6 are removed from the reaction chamber 7. Accordingly, a conjugate of the solid-phase antigen 6 and the antibody 3 remains in the reaction chamber 7.

Subsequently, the amount of the labeling substance 4 of the conjugate of the solid-phase antigen 6 and the antibody 3 that has remained in the reaction chamber 7 is measured. This measurement is carried out, for example, as follows. First, a solution containing a measuring reagent (for example, a substrate of the enzyme) that reacts with the labeling substance 4 is prepared. Next, this solution is introduced into the reaction chamber 7, and thereby a measurement solution is obtained that contains the measuring reagent and the conjugate of the solid-phase antigen 6 and the antibody 3. After the reaction between the measuring reagent and the labeling substance 4 is allowed to proceed in the measurement solution, a signal that reflects the amount of reaction product is detected.

As a result of this measurement, the amount of the antigen to be measured 2 in the sample solution 9 is calculated based on the amount of the solid-phase antigen 6 and the amount of the sample solution 9 introduced into the reaction chamber 7 in Step 1-B.

From the viewpoint of measuring the amount of the substance to be measured in the sample solution using a trace amount of sample solution in a short period of time, a chip-type biosensor is receiving attention. For example, JP 2 (1990)-062952 A discloses a chip-type biosensor including an insulating chip substrate, an electrode system disposed on the chip substrate, an enzyme reaction layer disposed on the electrode system, and an insulating layer that has notches and is disposed above the chip substrate in such a manner that the electrode system and the enzyme reaction layer are exposed. The enzyme reaction layer contains a measuring reagent for inducing an enzymatic cycling reaction, which is typified by an oxidoreductase and an electron mediator. An enzyme containing as a substrate the substance to be measured is used as the oxidoreductase. For example, glucose oxidase is used when the glucose amount is to be measured, and cholesterol oxidase is used when the cholesterol amount is to be measured. In this biosensor, a sample solution is dripped into the notches, so that the measuring reagent is dissolved in the sample solution. Thereby the reaction between the enzyme and the substance to be measured through an electron mediator (an enzymatic cycling reaction) proceeds. The amount of the substance to be measured in the sample solution is calculated based on the oxidation current value that is obtained by electrochemically oxidizing the electron mediator reduced by the enzyme reaction.

In the conventional immunological assay as shown in FIG. 1, as described above, Step 1-C is carried out using a wash solution typified by Tris-HCl buffer. Accordingly, in order to carry out the immunological assay on a chip, it is necessary to supply the wash solution from the outside of the chip or to allow the wash solution to be retained on the chip beforehand.

However, when the wash solution is supplied from the outside of the chip, extra time and effort is required for the supply. When the wash solution is allowed to be retained on the chip, this solution desirably is allowed to be retained on the chip in a hermetic state and in the state that facilitates it to be introduced into the reaction chamber for washing. However, it is not easy to form such a retaining state on a chip.

DISCLOSURE OF INVENTION

The present invention is intended to provide an immunological assay that does not require a wash solution typified by Tris-HCl buffer to be supplied from the outside of a chip or to have been retained on a chip beforehand and that is suitable for implementation on a chip. Furthermore, the present invention is intended to provide a chip that is suitable for the implementation of this immunological assay. The present invention also is intended to provide a measuring method using this chip.

Conventionally, in the immunological assay, it has been considered to be important to use a wash solution typified by Tris-HCl buffer that is free from substances to be measured such as protein, for washing of a reaction chamber. Surprisingly, however, the present inventor found that a signal reflecting the amount of the substance to be measured also was detected with excellent accuracy to an extent comparable to the case of using a wash solution, even by washing the reaction chamber using a biological sample containing the substance to be measured such as protein instead of the wash solution typified by Tris-HCl buffer.

The present invention provides a method of measuring, using a chip, the amount of antigen to be measured that is contained in a sample solution. The chip has a reaction chamber, a wash solution retaining chamber, an effluent chamber, and an injection port for injecting the sample solution. The injection port and the reaction chamber are connected to each other through a first channel. The injection port and the wash solution retaining chamber are connected to each other through a second channel. The wash solution retaining chamber and the reaction chamber are connected to each other through a third channel. Furthermore, the reaction chamber and the effluent chamber are connected to each other through a fourth channel. The method includes steps of injecting the sample solution from the injection port and dividing the sample solution into the reaction chamber and the wash solution retaining chamber through the first channel and the second channel, respectively; obtaining an antigen-antibody complex by allowing an antigen to be measured that is contained in the sample solution to bind to an antibody that specifically binds to the antigen to be measured, in the reaction chamber; separating the antigen-antibody complex and the antibody that has not bound to the antigen to be measured from each other by injecting the sample solution retained in the wash solution retaining chamber into the reaction chamber through the third channel and washing the reaction chamber including the antigen-antibody complex to leave one selected from i) the antigen-antibody complex and ii) the antibody that has not bound to the antigen to be measured, in the reaction chamber and moving the other into the effluent chamber; measuring the amount of the antigen-antibody complex or the antibody that has not bound to the antigen to be measured; and calculating the amount of the antigen to be measured that is contained in the sample solution, from the resultant amount of the antigen-antibody complex or the antibody that has not bound to the antigen to be measured.

From another aspect, the present invention provides a method of measuring the amount of antigen to be measured that is contained in a sample solution. The method includes: a binding step of obtaining an antigen-antibody complex by allowing the antigen to be measured to bind to an antibody that specifically binds to the antigen to be measured, in the reaction chamber; a washing and separating step of washing the reaction chamber with the sample solution to separate the antigen-antibody complex from the antibody that has not bound to the antigen to be measured; a measuring step of measuring the amount of the antigen-antibody complex or the antibody that has not bound to the antigen to be measured; and a step of calculating the amount of the antigen to be measured that is contained in the sample solution from the resultant amount of the antigen-antibody complex or the antibody that has not bound to the antigen to be measured.

From another aspect, the present invention provides a chip for measuring the amount of an antigen to be measured that is contained in the sample solution. The chip has a reaction chamber, a wash solution retaining chamber, an effluent chamber, and an injection port for injecting the sample solution. The injection port and the reaction chamber are connected to each other through a first channel. The injection port and the wash solution retaining chamber are connected to each other through a second channel. The wash solution retaining chamber and the reaction chamber are connected to each other through a third channel. Furthermore, the reaction chamber and the effluent chamber are connected to each other through a fourth channel. In the chip, the sample solution injected from the injection port flows into the reaction chamber and the wash solution retaining chamber through the first channel and the second channel, respectively. In the reaction chamber, the antigen to be measured is allowed to bind to an antibody that specifically binds to the antigen to be measured and thereby an antigen-antibody complex is obtained. Then the sample solution retained in the wash solution retaining chamber is injected into the reaction chamber through the third channel to wash the reaction chamber containing the antigen-antibody complex. Thus, one selected from i) the antigen-antibody complex and ii) the antibody that has not bound to the antigen to be measured is left in the reaction chamber and the other moves into the effluent chamber. Thus the antigen-antibody complex and the antibody that has not bound to the antigen to be measured are separated from each other.

According to the present invention, the reaction chamber can be washed to an extent that allows a signal, which reflects the amount of substance to be measured, to be detected, without using a wash solution typified by Tris-HCl buffer when the immunological assay is carried out.

DESCRIPTION OF THE PREFERRED EMBODIMENTS

Figure 1:
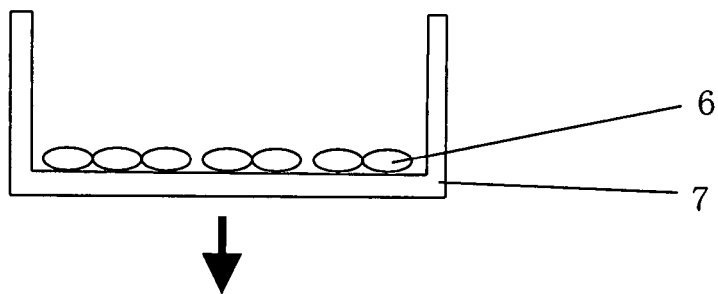
FIG. 1 is a flow chart for explaining one example of conventional immunological assays.
Figure 1:
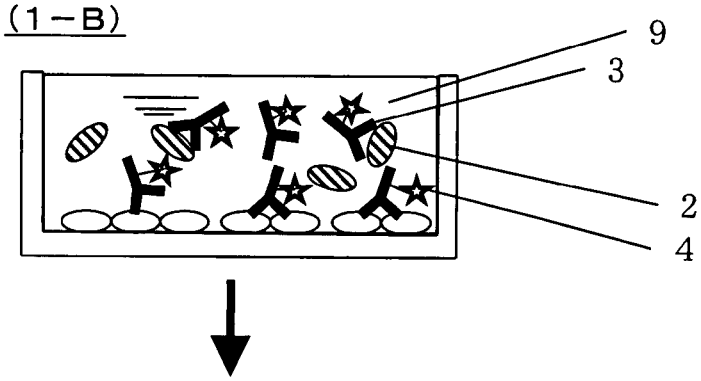
Figure 1:
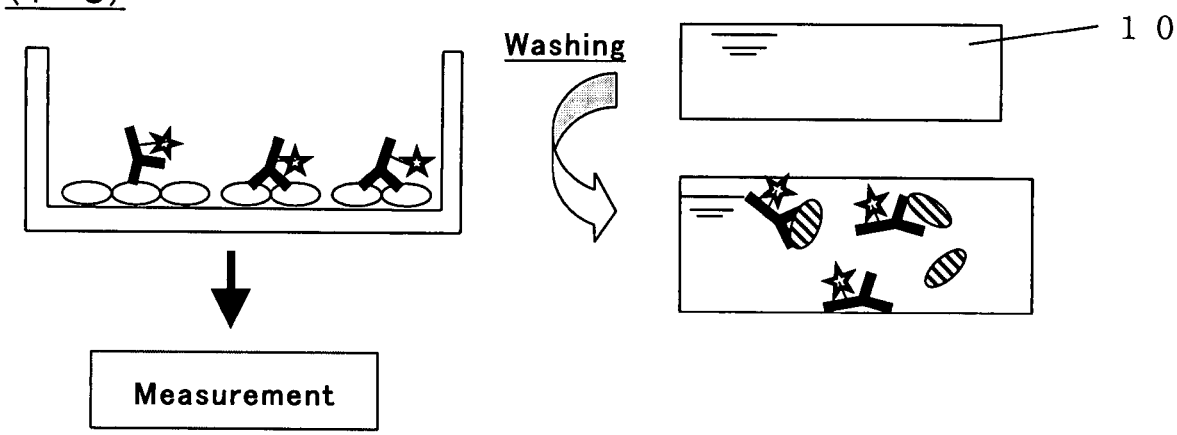
Figure 2:
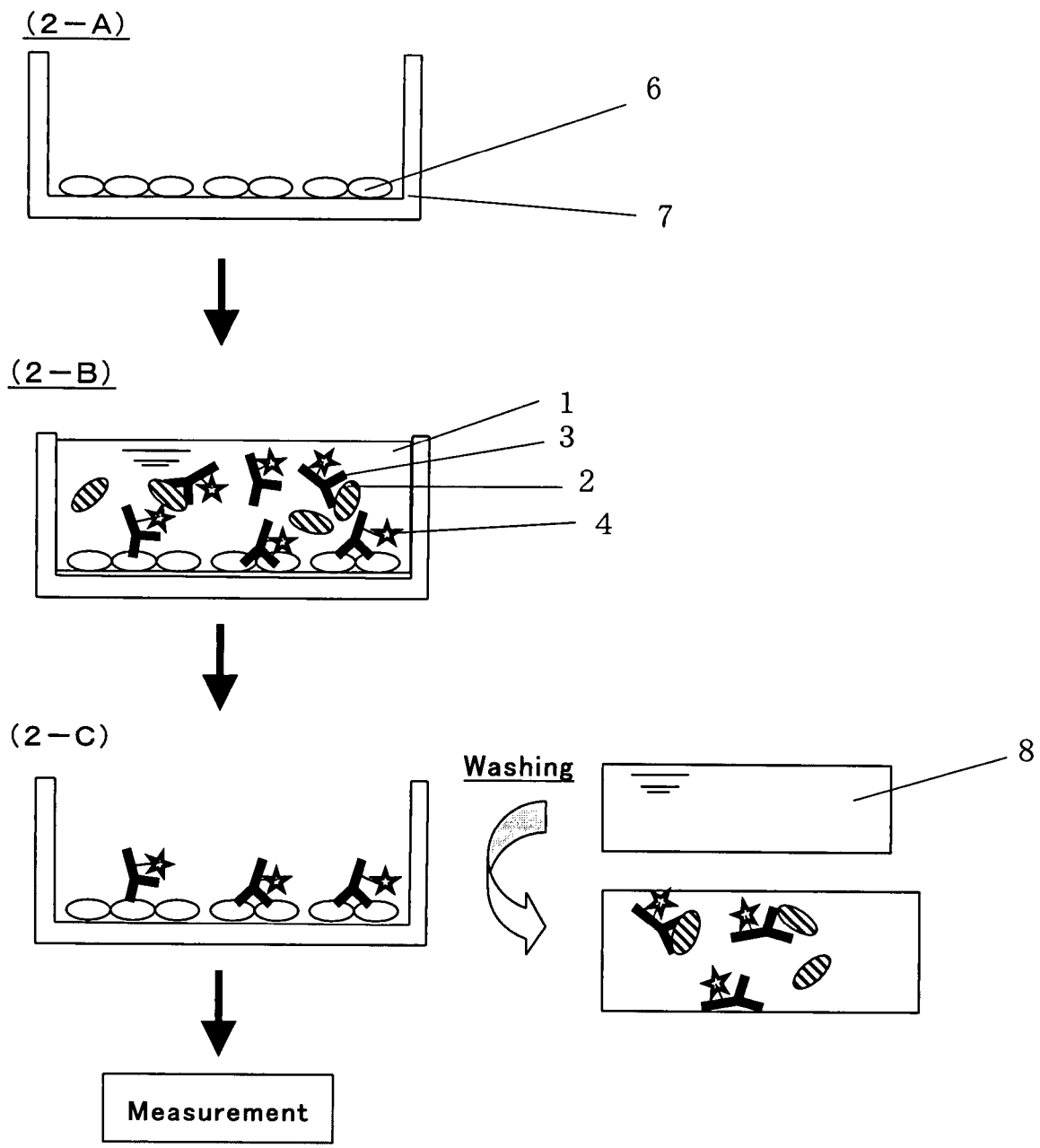
FIG. 2 is a flow chart for explaining one example of the immunological assays according to the present invention.

An example of the immunological assay according to the present invention is described with reference to the flow chart shown in FIG. 2.

<Step 2-A: Forming a Solid-Phase Antigen>

A solid-phase antigen 6 is formed by fixing a predetermined amount of capture antigen having an epitope identical to that of a specific protein (an antigen to be measured 2) contained in a sample solution, to the surface of a reaction chamber 7. The fixation of the capture antigen can be carried out, for example, in the same manner as in Step 1-A employed in the conventional ELISA.

Examples of the material for the reaction chamber 7 include resins such as polystyrene, polyethylene terephthalate (PET), polycarbonate, and polydimethylsiloxane, glass, and magnetic materials. The reaction chamber 7 desirably has a shape capable of retaining a liquid, such as a tube type or a well type typified by a microplate.

<Step 2-B: Binding Step>

A predetermined amount of part 1 of the sample solution is dispensed. Examples of the sample solution include biological liquid samples such as blood, urine, saliva, sweat, and tear. An antibody 3 labeled with a labeling substance 4 is added to the part 1 of the sample solution. The antibody 3 is a primary antibody that specifically binds to the antigen to be measured 2. The other part 8 of the sample solution is reserved, with the antibody 3 being not added thereto. The antibody 3 can be a commercially available one or one prepared originally using a laboratory animal. The antibody 3 can be a polyclonal antibody but is preferably a monoclonal antibody from the viewpoint of improving the specificity and sensitivity of the antigen-antibody reaction. Example of the antigen to be measured 2 include proteins that is receiving high clinical attention, such as C-reactive protein (CRP), serum amyloid A, troponin T, creatine kinase MB, and retinol-binding protein. The labeling substance 4 is preferably an enzyme but can be a fluorescent dye or further a radioisotope.

The part 1 of the sample solution in the state immediately after the labeled antibody 3 is added thereto is introduced into the reaction chamber 7 to which the solid-phase antigen 6 has been fixed. With this operation, the part 1 of the sample solution is introduced into the reaction chamber 7. The part 1 of the sample solution after being introduced is maintained in the reaction chamber 7 at a predetermined temperature for a predetermined period of time. Thereby an antigen-antibody reaction proceeds competitively between the antibody 3 and the solid-phase antigen 6 as well as the antigen to be measured 2, and an antigen-antibody complex that is a conjugate of the antigen to be measured 2 and the antibody 3 as well as a conjugate of the solid-phase antigen 6 and the antigen 3 are formed in the reaction chamber 7. Since the conjugate of the solid-phase antigen 6 and the antibody 3 has not bound to the antigen to be measured 2, the conjugate is handled as "an antibody that has not bound to the antigen to be measured" as in the case of the antibody 3 in the present specification. As described above, the immunological assay of the present invention can be arranged as follows. That is, the solid-phase antigen is fixed to the reaction chamber and the antigen-antibody complex and the antibody that has not bound to the antigen to be measured, which has bound to the solid-phase antigen, are obtained in the binding step.

The antigen-antibody reaction that occurs in the reaction chamber 7 can be a noncompetitive reaction. The noncompetitive reaction can be obtained as follows. The part 1 of the sample solution to which the labeled antibody 3 has been added is maintained at a predetermined temperature for a predetermined period of time before being introduced into the reaction chamber 7. After the reaction between the antigen to be measured 2 and the labeled antibody 3 is allowed to reach a steady state, the part 1 of the sample solution is introduced into the reaction chamber 7. The antibody 3 that has not bound to the antigen to be measured 2 and the solid-phase antigen 6 are then allowed to react with each other. In this manner, the noncompetitive reaction can proceed. The temperature and period of time for allowing the antigen-antibody reaction to proceed can be set suitably according to the type of the antigen and antibody. The same applies to the following antigen-antibody reaction.

<Step 2-C: Washing and Separating Step>

Using the other part 8 of the sample solution that has been reserved in the binding step (Step 2-B), the reaction chamber 7 is washed. This washing can be carried out as follows, for example. First, with a pipette, the part 1 of the sample solution in the reaction chamber 7 is removed. Subsequently, the other part 8 of the sample solution is dripped into the reaction chamber 7 with the pipette and pipetting is carried out for a few times. Thereafter the other part 8 of the sample solution is removed from the reaction chamber 7. Thus the antigen-antibody complex is removed from the reaction chamber 7 and the antibody that has not bound to the antigen to be measured remains. Accordingly, the antigen-antibody complex and the antibody that has not bound to the antigen to be measured, which are obtained in the binding step (Step 2-B), are separated from each other. Thus, the reaction chamber can be washed using the sample solution without using a wash solution typified by Tris-HCl buffer. As described above, conventionally it is considered to be important to use a wash solution typified by Tris-HCl buffer for washing the reaction chamber. This is intended to separate the antigen-antibody complex and the antibody that has not bound to the antigen to be measured from each other without impurity contamination. However, even when the reaction chamber is washed with a sample solution as described above, the antigen-antibody complex and the antibody that has not bound to the antigen to be measured seem to be able to be separated from each other with high accuracy, since as described later in Example, a signal reflecting the amount of the substance to be measured can be detected with excellent accuracy to an extent comparable to the case where the reaction chamber is washed with a wash solution typified by Tris-HCl buffer.

<Measuring Step>

The amount of the labeling substance 4 in the antibody that has not bound to the antigen to be measured and that has remained in the reaction chamber 7 is measured. This measurement can be carried out, for example, as follows. First, a solution containing a measuring reagent is prepared. The measuring reagent can be selected according to the type of the labeling substance 4. For instance, when the labeling substance 4 is an enzyme, it can be the substrate of the enzyme. Subsequently, the solution is introduced into the reaction chamber 7, and thereby a measurement solution containing the measuring reagent and the antibody that has not bound to the antigen to be measured is obtained in the reaction chamber 7. In the measurement solution, the reaction between the measuring reagent and the labeling substance 4 in the antibody that has not bound to the antigen to be measured is allowed to proceed. Thereafter, the amount of signal reflecting the amount of the reaction product is detected using, for example, a known optical measuring means or electrochemical measuring means.

<Calculating Step>

Based on the measurement result obtained in the measuring step, the amount of the antigen to be measured is calculated. More specifically, the amount of the antigen to be measured 2 is calculated based on the amount of the solid-phase antigen 6 that has been fixed to the reaction chamber 7 and the amount of the part 1 of the sample solution that was introduced into the reaction chamber in the binding step (Step 2-B) that are obtained as result of the measurement described above. The amount of the antigen to be measured can be expressed as a physical quantity that can be associated with the above-mentioned amount, for example, the concentration. Thus the amount of the antigen to be measured that is contained in the sample solution is calculated from the amount of the antibody that has not bound to the antigen to be measured or the amount of the antigen-antibody complex as described later, which has been measured in the measuring step.

Figure 5:
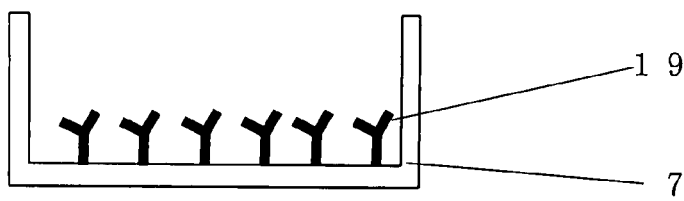
FIG. 5 is a flow chart for explaining one example in which an antigen-antibody reaction between an antibody and an antigen to be measured is carried out by a sandwich method.
Figure 5:
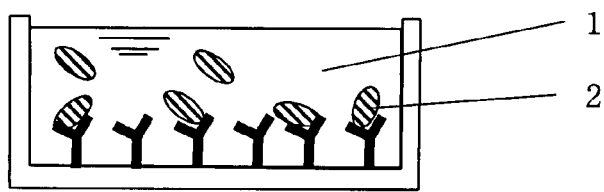
Figure 5:
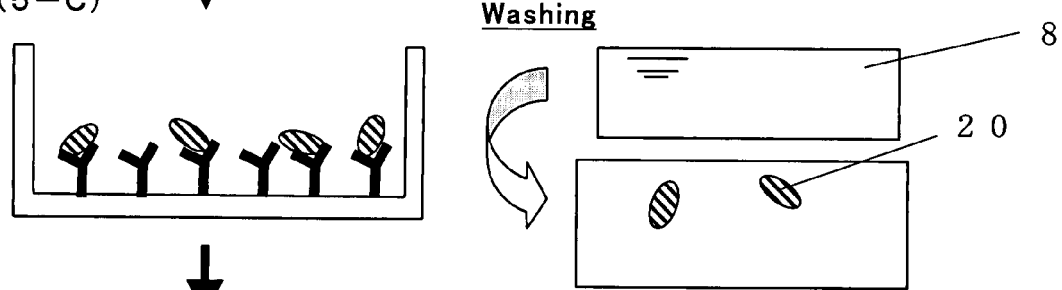
Figure 5:
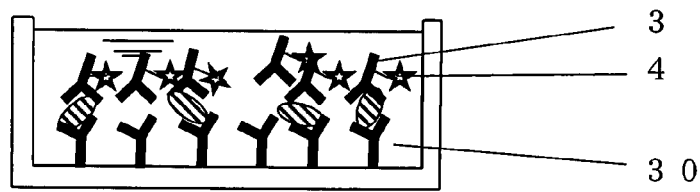
Figure 5:
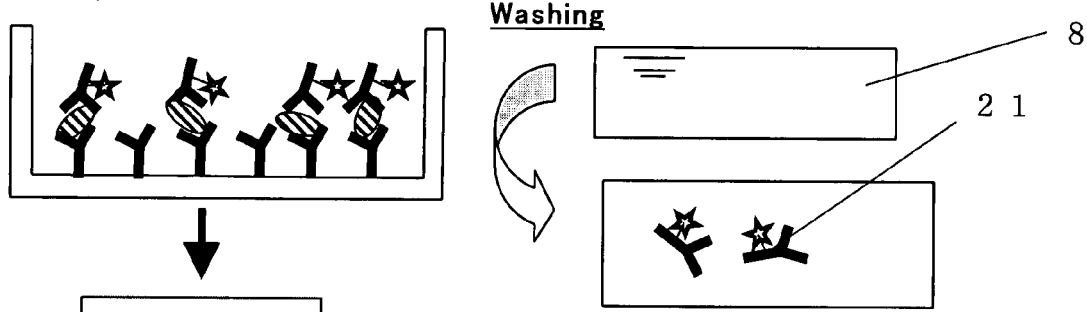

Another example of the immunological assay according to the present invention is described with reference to the step diagram shown in FIG. 5. In this example, the antigen-antibody reaction between an antibody and an antigen to be measured is carried out by the sandwich method.

<Step 5-A: Forming a Solid-Phase Antibody>

A predetermined amount of capture antibody to bind to an antigen to be measured 2 that is contained in a sample solution is fixed to the surface of the reaction chamber 7 and thereby a solid-phase antibody 19 is formed. The fixation of the capture antibody can be carried out, for example, in the same manner as in Step 2-A in the immunological assay shown in FIG. 2.

<Steps 5-B to 5-D: Binding Step>

A predetermined amount of sample solution is dispensed. Thus, a part 1 of the sample solution and the other part 8 of the sample solution are prepared.

The part 1 of the sample solution is introduced into the reaction chamber 7 to which the solid-phase antibody 19 has been fixed (Step 5-B).

With this operation, the part 1 of the sample solution is introduced into the reaction chamber 7. The part 1 of the sample solution thus introduced is maintained in the reaction chamber 7 at a predetermined temperature for a predetermined period of time. Thus, an antigen-antibody reaction proceeds between the solid-phase antibody 19 and the antigen to be measured 2, and a conjugate of the antigen to be measured 2 and the solid-phase antibody 19 is formed in the reaction chamber 7.

Subsequently, the reaction chamber 7 is washed with the other part 8 of the sample solution (Step 5-C). In this step, not all of the other part 8 of the sample solution is used and the rest is kept so as to be used in the washing and separating step (Step 5-E) described later. This washing (Step 5-C) can be carried out in the same manner as in Step 2-C employed in the immunological assay shown in FIG. 2. However, since the other part 8 of the sample solution contains the antigen to be measured 2, it is desirable to remove it from the reaction chamber 7 quickly enough to prevent the antigen-antibody reaction from proceeding between the antigen to be measured 2 and the solid-phase antibody 19. In this washing (Step 5-C), the antigen to be measured 2 that has not bound to the solid-phase antibody 19 in Step 5-B is removed from the reaction chamber 7. Thus a conjugate of the antigen to be measured 2 and the solid-phase antibody 19 remains in the reaction chamber 7.

Thereafter, a solution 30 is introduced into the reaction chamber 7. The solution 30 is prepared by adding a predetermined amount of antibody 3 labeled with a labeling substance 4 to a solvent free from protein having an epitope identical to that of the antigen to be measured 2. The antibody 3 to be used herein is a primary antibody that also can bind to the antigen to be measured 2 that has bound to the solid-phase antibody 19. An example of the solvent for the solution 30 is Tris-HCl buffer. The solution 30 introduced as described above is maintained in the reaction chamber 7 at a predetermined temperature for a predetermined period of time (Step 5-D). Thus, an antigen-antibody reaction proceeds between the labeled antibody 3 and the antigen to be measured 2 that has bound to the solid-phase antibody 19. This antigen-antibody reaction gives an antigen-antibody complex that is a conjugate of the solid-phase antibody 19, the antigen to be measured 2 and the antibody 3, as well as the antibody that has not bound to the antigen to be measured and that is the remainder 21 of the labeled antibody 3. The remainder 21 of the antibody 3 is present in the solution 30 in the state of being released from the surface of the reaction chamber 7.

The immunological assay of the present invention can be arranged as follows. That is, the solid-phase antibody is disposed in the reaction chamber, the solid-phase antibody and the antigen to be measured are allowed to bind to each other in the binding step, further a part of the antibody is allowed to bind to the antigen to be measured that has bound to the solid-phase antibody, and thereby an antigen-antibody complex that is a conjugate of the solid-phase antibody, the antigen to be measured and the above-mentioned part of the antibody, as well as the antibody that has not bound to the antigen to be measured and that is the remainder of the antibody are obtained.

<Step 5-E: Washing and Separating Step>

The reaction chamber 7 is washed with the other part 8 of the sample solution that has been reserved in Step 5-C. This washing can be carried out in the same manner as in Step 2-C employed in the immunological assay shown in FIG. 2. Thus, the antibody that has not bound to the antigen to be measured is removed from the reaction chamber 7, and the antigen-antibody complex remains in the reaction chamber 7. In this manner, by washing the reaction chamber using the sample solution, the antigen-antibody complex and the antibody that has not bound to the antigen to be measured, which have been obtained in Step 5-D, are separated from each other without using a wash solution typified by Tris-HCl buffer. The separation accuracy also is considered to be excellent to an extent comparable to the case where the reaction chamber is washed using a wash solution typified by Tris-HCl buffer.

<Measuring Step>

The amount of the labeling substance 4 in the antigen-antibody complex that has remained in the reaction chamber 7 is measured. This measurement can be carried out in the same manner as in the measuring step employed in the immunological assay shown in FIG. 2.

<Calculating Step>

Based on the measurement result obtained in the measuring step, the concentration of the antigen to be measured is calculated. More specifically, based on the measurement result, i.e. the amount of the solid-phase antibody 19 fixed to the reaction chamber 7 and the amount of the part 1 of the sample solution introduced into the reaction chamber 7 in the binding step (Step 5-B), the amount of the antigen to be measured 2 is calculated. The amount of the antigen to be measured can be expressed as a physical quantity that can be associated with the above-mentioned amount, for example, the concentration.

Figure 3:
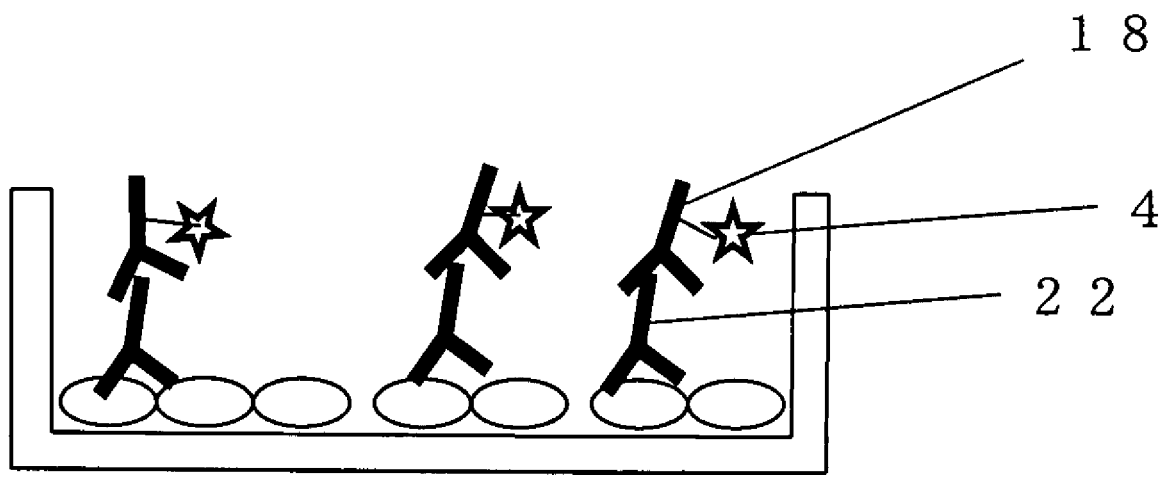
FIG. 3 is a diagram for explaining one example of the immunological assays according to the present invention that is carried out using an unlabeled primary antibody and a labeled secondary antibody.

In the immunological assay of the present invention, the operation and equipment to be used therein can be changed suitably as long as a signal reflecting the concentration of the substance to be measured can be detected to an extent comparable to the case of using a wash solution typified by Tris-HCl buffer. For example, in the immunological assays shown in FIGS. 2 and 5, the descriptions were made about the case where the primary antibody used for obtaining an antigen-antibody complex or an antibody that had not bound to an antigen to be measured was labeled with a labeling substance. Instead of this, however, as shown in the conceptual diagram in FIG. 3, a primary antibody 22 used for obtaining an antigen-antibody complex or an antibody that has not bound to an antigen to be measured is not labeled but a secondary antibody 18 that is allowed to bind to the unlabeled primary antibody 22 can be labeled with a labeling substance. Furthermore, in the immunological assays shown in FIGS. 2 and 5, the description was made about the case where the measuring step was carried out with respect to one selected from the antigen-antibody complex and the antibody that had not bound to the antigen to be measured, which remained in the reaction chamber 7 after the washing and separating step. Instead of this, however, the measuring step can be carried out with respect to the other selected from the antigen-antibody complex and the antibody that has not bound to the antigen to be measured, which have been removed from the reaction chamber 7 in the washing and separating step. Furthermore, in the immunological assay of the present invention, as described above, from the viewpoint of facilitating the implementation on a chip, it is desirable to use as the reaction chamber a chip substrate having a shape capable of retaining a liquid that is typified by a microplate. However, it is not excluded to use, instead of this, a chip substrate having a shape that does not allow a liquid to be retained easily, which is typified by beads such as resin beads and magnetic beads. In the immunological assays shown in FIGS. 2 and 5, the descriptions were made about the case where the sample solution was dispensed and thereby the solution for inducing the antigen-antibody reaction in the reaction chamber and the solution for washing the reaction chamber were prepared. Instead of this, however, a solution for washing can be prepared by newly collecting a sample solution.

Figure 4:
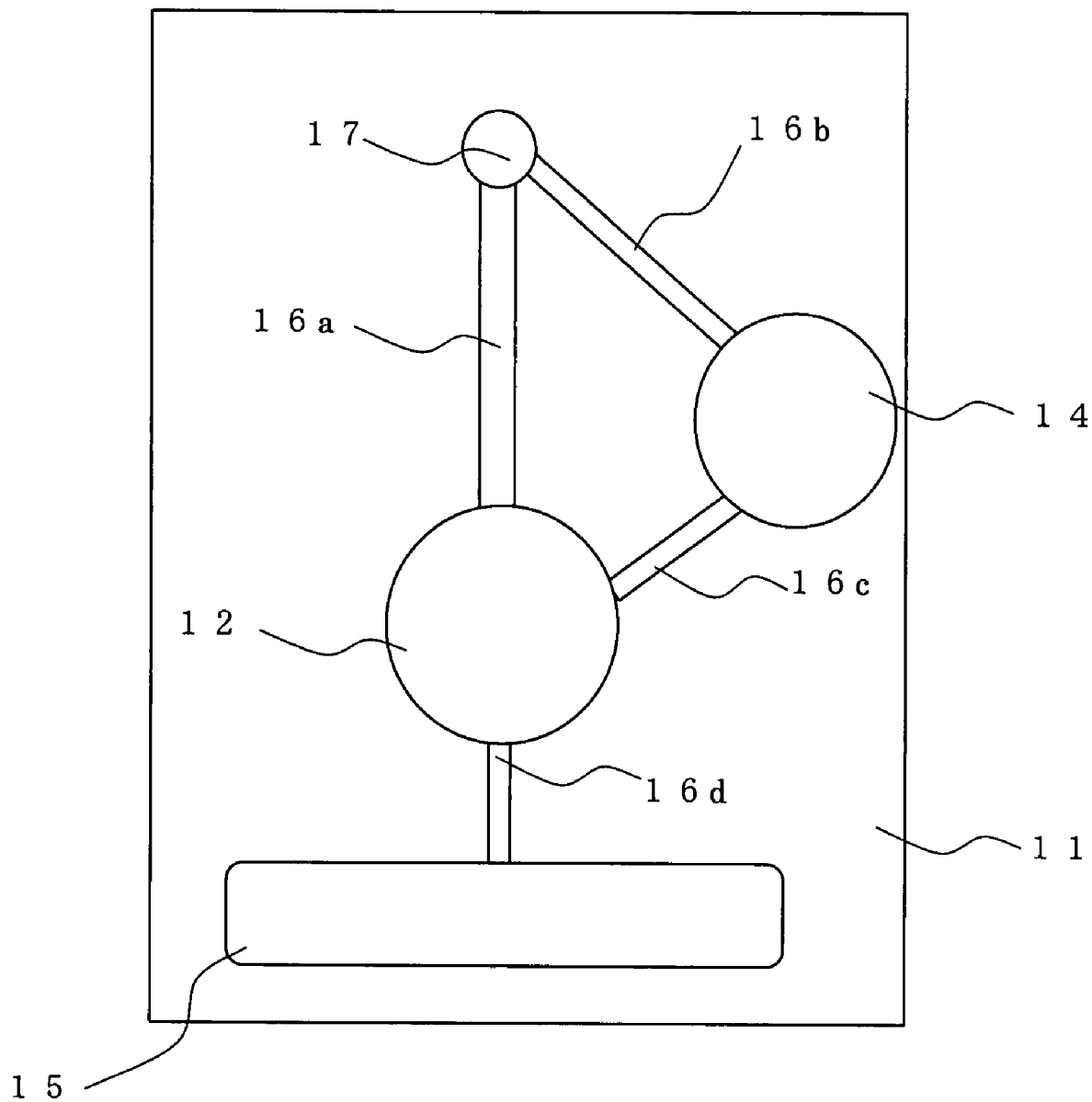
FIG. 4 is a diagram for explaining one example of the chips according to the present invention.

FIG. 4 is a diagram for explaining an example of the chip suitable for carrying out the immunological assay of the present invention.

The chip 100 includes: a chip substrate 11; and a reaction chamber 12, a wash solution retaining chamber 14, an effluent chamber 15, and an injection port 17 through which a sample solution is injected, which are formed in the substrate 11. Examples of the material for the chip substrate 11 include materials for the reaction chamber 7 that are used in the immunological assays of the present invention, which is typified by PET.

The injection port 17 and the reaction chamber 12 are connected to each other through a channel 16a formed in the chip substrate 11. Furthermore, the injection port 17 and the wash solution retaining chamber 14 are connected to each other through a channel 16b formed in the chip substrate 11. The channel 16a and the channel 16b are not in communication with each other. Accordingly, when a sample solution is injected into the injection port 17, the sample solution is divided to flow into the reaction chamber 12 and the wash solution retaining chamber 14 through the channel 16a and the channel 16b, respectively. Thus, a part of the sample solution is sent to the reaction chamber 12 and the other part of the sample solution is sent to the wash solution retaining chamber 14 and is retained in the chamber 14.

It is desirable that either one of (1) a solid-phase antigen and (2) a solid-phase antibody be fixed to the reaction chamber 12. It is desirable that a primary antibody that specifically binds to an antigen to be measured in the sample solution be placed inside the reaction chamber 12 or on the path through which the part of the sample solution passes until it is introduced into the reaction chamber 12, in the state of being able to be dissolved in the sample solution. The primary antibody is preferably in the state of having been labeled with a labeling substance. When the part of the sample solution is introduced into the reaction chamber 12, (1) an antigen-antibody complex that is a conjugate of the antigen to be measured and the antibody, as well as an antibody that has not bound to the antigen to be measured and that is a conjugate of a solid-phase antigen and the antibody are obtained in the case where the solid-phase antigen has been fixed to the reaction chamber 12, and (2) an antigen-antibody complex that is a conjugate of the solid-phase antibody, the antigen to be measured and the antibody, as well as an antibody that has not bound to the antigen to be measured and that is the remainder of the antibody are obtained in the case where the solid-phase antibody has been fixed to the reaction chamber 12.

The reaction chamber 12 and the effluent chamber 15 are connected to each other through a channel 16d formed in the chip substrate 11. Furthermore, the wash solution retaining chamber 14 and the reaction chamber 12 are connected to each other through a channel 16c formed in the chip substrate 11. The sample solution (the above-mentioned other part) retained in the wash solution retaining chamber 14 is injected into the reaction chamber 12 through the channel 16c after the antigen-antibody reaction reaches the steady state in the reaction chamber 12. Further, it is sent from the reaction chamber 12 to the effluent chamber 15 through the channel 16d. Thus, the antibody that has not bound to the antigen to be measured and that is a conjugate of the solid-phase antigen and the antibody remains in the reaction chamber 12 in the case where the solid-phase antigen is placed in the reaction chamber 12, while the antigen-antibody complex that is a conjugate of the solid-phase antibody, the antigen to be measured and the antibody remains in the reaction chamber 12 in the case where the solid-phase antibody is placed in the reaction chamber 12. Accordingly, when the reaction chamber 12 is washed with the sample solution, the antigen-antibody complex and the antibody that has not bound to the antigen to be measured are separated from each other.

As described above, the chip of the present invention can be arranged as follows. That is, the solid-phase antigen is fixed to the reaction chamber, the antibody that has not bound to the antigen to be measured has bound to the solid-phase antigen, the antibody that has not bound to the antigen to be measured is left in the reaction chamber by the washing, and the antigen-antibody complex moves into the effluent chamber. Furthermore, as described above, in the chip of the present invention, the solid-phase antibody is fixed to the reaction chamber, the antigen-antibody complex is a conjugate of the solid-phase antibody, the antigen to be measured and the antibody, the antigen-antibody complex is left in the reaction chamber by the washing, and the antibody that has not bound to the antigen to be measured moves into the effluent chamber.

The solution can be sent through the respective channels by a known method of sending a solution, such as a method utilizing electroosmotic flow (for example, Barker et al., Anal. Chem.; (Article); 2000; 72(24); 5925-5929), a method utilizing injection force or suction power that is provided by a pump (for instance, Hisamoto et al., Anal. Chem.; (Article); 2001; 73(22); 5551-5556), and a method utilizing centrifugal force (for instance, Duffy et al., Anal. Chem.; (Article); 1999; 71(24); 4669-4678).

As described above, with the chip of the present invention, it is possible to separate the antigen-antibody complex and the antibody that has not bound to the antigen to be measured from each other even when using no wash solution typified by Tris-HCl buffer. As described in the explanation of the immunological assays according to the present invention, the separation accuracy is high. Accordingly, the chip of the present invention allows a signal reflecting the concentration of the substance to be measured to be detected to an extent comparable with the case of using a wash solution typified by Tris-HCl buffer. The detection of the signal can be carried out with respect to one selected from the antigen-antibody complex left in the reaction chamber 12 and the antibody that has not bound to the antigen to be measured, or with respect to the other that was moved to the effluent chamber 15. In this manner, the effluent chamber also can be used for implementation of an enzyme reaction in addition to effluent storage, and the intended use thereof is not limited by the term "effluent".

The chip of the present invention can be changed suitably in design as long as measurement can be carried out suitably well to an extent comparable to the case of using a wash solution typified by Tris-HCl buffer. For instance, another channel for introducing a labeled antibody into the reaction chamber can be formed additionally so that the antigen-antibody reaction can be implemented by the sandwich method.

Hereinafter, the present invention is described further in detail using examples.

Reference Example

First, a reference example is described, in which a reaction chamber was washed using a buffer solution (Tris-HCl buffer) after the antigen-antibody reaction had occurred.

[Preparation of Sample Solution]

Normal human serum was mixed with a 42.3-μM CRP solution and thereby sample solutions with CRP concentrations of approximately 0 nM, 10 nM, 20 nM, 50 nM, and 100 nM were prepared.

[Production of Reaction Chamber]

A plurality of holes with a diameter of 5 mm were formed in a 1-mm thick PET sheet. Another PET sheet was attached to one surface of the above-mentioned PET sheet using a known light curing adhesive (LUXTRAK) so as to cover one ends of the holes. Thus a plurality of reaction chambers were produced.

[Fixation of CRP]

Using 50-mM Tris-HCl buffer (pH 7.5), a 42.3-nM CRP solution was prepared. 10 μl of the CRP solution was introduced into each of the respective reaction chambers. Subsequently, each reaction chamber was sealed with a resin sheet (a sheet for 96 holes). This was maintained at 35° C. for one hour and thereby the CRP was allowed to adsorb to the reaction chambers. Thereafter, the reaction chambers were washed with 50-mM Tris-HCl buffer (pH 7.5). Subsequently, 10 μl of blocking agent (manufactured by SEIKAGAKU CORPORATION, AppliEDuo, CatNo. 200140) was added to each reaction chamber. This was maintained at 35° C. for one hour. Thus the CRP allowed to adsorb to the reaction chamber was blocked and a solid-phase antigen was formed in the reaction chamber. Thereafter, the reaction chambers were washed again with 50-mM Tris-HCl buffer (pH 7.5).

[Antigen-Antibody Reaction]

1 μl of 880-nM anti-CRP monoclonal antibody that had been labeled with alkaline phosphatase (ALP), 1 μl of sample solution, and 8 μl of human normal serum were introduced into reaction chambers. This was maintained at 35° C. for 15 minutes. Thus the antigen-antibody reactions between the antibody and the solid-phase antigen as well as CRP were allowed to proceed. The final concentration of the antibody in each reaction chamber was 88 nM. The final CRP concentrations were about 0 nM, 10 nM, 20 nM, 50 nM, and 100 nM.

[Washing and Separating]

After 20 μl of wash solution was introduced into the reaction chambers, it was removed. The wash solution used herein was 50-mM Tris-HCl buffer (pH 7.5). Thus the reaction chambers were washed and thereby the antigen-antibody complex that was a conjugate of CRP and the antibody was separated from the antibody that had not bound to the antigen to be measured and that was a conjugate of the solid-phase antigen and the antibody. More specifically, the antigen-antibody complex was removed from the reaction chambers, while the antibody that had not bound to the antigen to be measured was left in the reaction chambers.

[Measurement]

10 μl of p-nitrophenylphosphate solution (manufactured by Cygnus, PNPP Liquid Substrate, CatNo. F008-1000; pNPP) was introduced into each reaction chamber. Thereby the enzyme reaction was allowed to proceed between pNPP and ALP of the antibody that had not bound to the antigen to be measured. The product of the enzyme reaction, p-nitrophenol (pNP) was measured for absorbance from each reaction chamber.

Example

An immunological assay was carried out in the same manner as in the reference example except that the reaction chambers were washed after the antigen-antibody reaction using 20 μl of sample solution instead of the wash solution. The sample solution used for washing was prepared by dispensing the sample solution for inducing the antigen-antibody reaction.

Comparative Example

An immunological assay was carried out in the same manner as in the reference example except that the reaction chambers were not washed after the antigen-antibody reaction. More specifically, while the wash solution that had been introduced therein was not removed, pNP was further introduced into the reaction chambers and the absorbance was measured.

Figure 6:
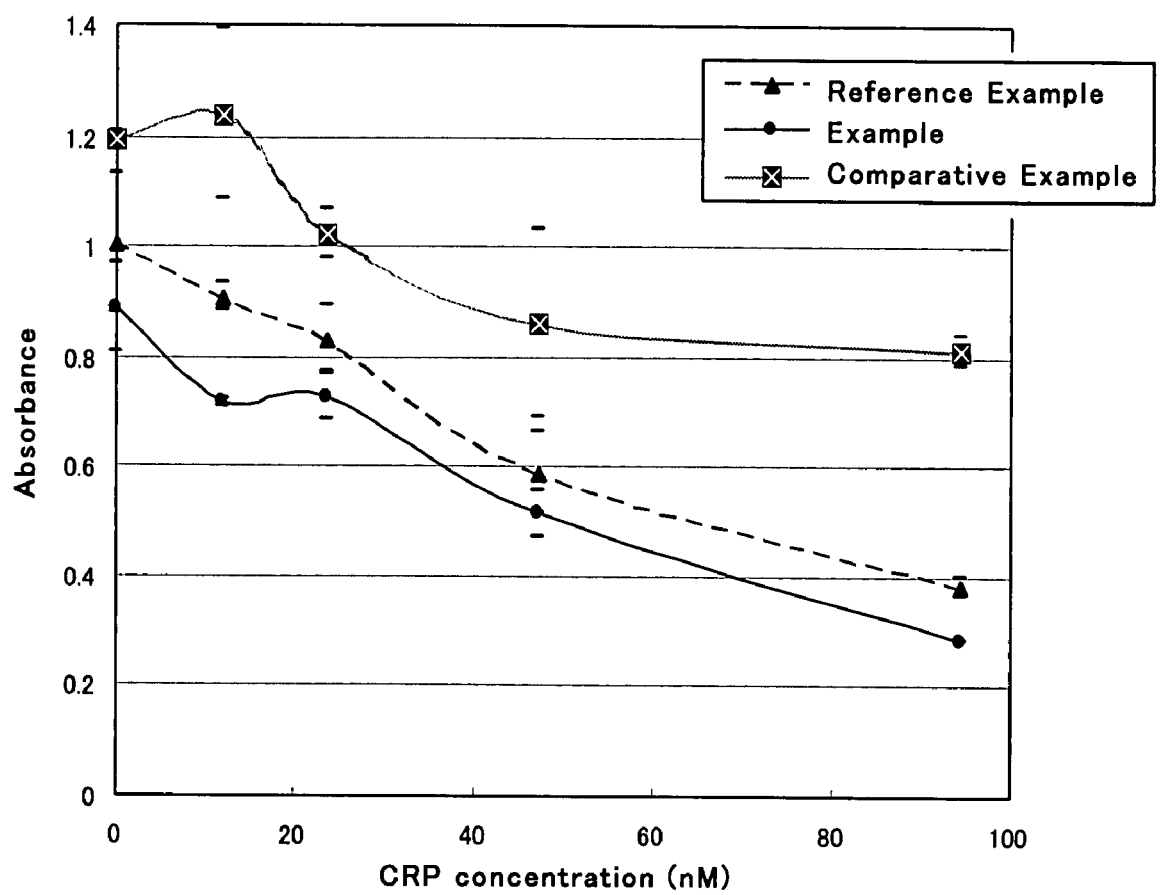
FIG. 6 is a graph showing the result of absorbance measurement.

FIG. 6 is a graph showing the measurement results of absorbance obtained from each example. The absorbance is expressed as a relative value, with the absorbance obtained from the reaction chamber in which the final CRP concentration was about 0 nM in the reference example being 1.

Table 1 shows the evaluation results of the background of and variations in each absorbance based on the graph shown in FIG. 6. The evaluation of the background of absorbance was expressed as follows:

⊚: the absolute value of the average value dropped most after washing,

○: it dropped the second most after washing, and x: it was fully affected by the background.

The evaluation of the variations in absorbance was expressed as follows:

⊚: the smallest standard deviation,

○: a slightly larger standard deviation than the above, and x: a clearly larger than those.

TABLE 1

|  | Reference Example | Example | Comparative Example |
|---|---|---|---|
| Background | ○ | ⊚ | X |
| Variations | ⊚ | ○ | X |

As shown in Table 1, it was proved that an excellent washing effect was obtained to an extent comparable to the case of using a wash solution typified by Tris-HCl buffer even when using the sample solution for washing the reaction chambers.

INDUSTRIAL APPLICABILITY

The present invention provides an immunological assay in which a wash solution typified by Tris-HCl buffer does not need to be supplied from the outside of a chip or to be retained on the chip beforehand. Therefore, the present invention has a great deal of potential in each field where the immunological assay is required to be carried out on a chip.

What is claimed is:

1. A method of measuring, using a chip, the amount of an antigen to be measured that is contained in a sample solution, wherein the chip comprises a reaction chamber, a wash solution retaining chamber, an effluent chamber, and an injection port for injecting the sample solution, the injection port and the reaction chamber are connected to each other through a first channel, the injection port and the wash solution retaining chamber are connected to each other through a second channel, the wash solution retaining chamber and the reaction chamber are connected to each other through a third channel, the reaction chamber and the effluent chamber are connected to each other through a fourth channel, the method comprises steps of:

injecting the sample solution from the injection port and dividing the sample solution into the reaction chamber and the wash solution retaining chamber through the first channel and the second channel, respectively;

obtaining an antigen-antibody complex by allowing an antigen to be measured that is contained in the sample solution to bind to an antibody that specifically binds to the antigen to be measured, in the reaction chamber;

separating the antigen-antibody complex and the antibody that has not bound to the antigen to be measured from each other by injecting the sample solution retained in the wash solution retaining chamber into the reaction chamber through the third channel and washing the reaction chamber including the antigen-antibody complex to leave one selected from:

i) the antigen-antibody complex; and ii) the antibody that has not bound to the antigen to be measured, in the reaction chamber and to move the other into the effluent chamber;

measuring the amount of the antigen-antibody complex or the antibody that has not bound to the antigen to be measured; and calculating the amount of the antigen to be measured that is contained in the sample solution, from the resultant amount of the antigen-antibody complex or the antibody that has not bound to the antigen to be measured.

2. The method according to claim 1, wherein a solid-phase antigen has been fixed to the reaction chamber, the antibody that has not bound to the antigen to be measured has bound to the solid-phase antigen, and in the step of separation, the antibody that has not bound to the antigen to be measured is left in the reaction chamber while the antigen-antibody complex moves into the effluent chamber.

3. The method according to claim 1, wherein a solid-phase antibody has been fixed to the reaction chamber, the antigen-antibody complex is a conjugate of the solid-phase antibody, the antigen to be measured and the antibody, and in the step of separation, the antigen-antibody complex is left in the reaction chamber while the antibody that has not bound to the antigen to be measured moves into the effluent chamber.

4. A chip for measuring the amount of an antigen to be measured that is contained in a sample solution, wherein the chip comprises a reaction chamber, a wash solution retaining chamber, an effluent chamber, and an injection port for injecting the sample solution, the injection port and the reaction chamber are connected to each other through a first channel, the injection port and the wash solution retaining chamber are connected to each other through a second channel, the wash solution retaining chamber and the reaction chamber are connected to each other through a third channel, the reaction chamber and the effluent chamber are connected to each other through a fourth channel, the sample solution injected from the injection port flows into the reaction chamber and the wash solution retaining chamber through the first channel and the second channel, respectively, in the reaction chamber, the antigen to be measured is allowed to bind to an antibody that specifically binds to the antigen to be measured and thereby an antigen-antibody complex is obtained, the sample solution retained in the wash solution retaining chamber is injected into the reaction chamber through the third channel to wash the reaction chamber containing the antigen-antibody complex, so that one selected from:

i) the antigen-antibody complex; and ii) the antibody that has not bound to the antigen to be measured is left in the reaction chamber and the other moves into the effluent chamber, and thereby the antigen-antibody complex and the antibody that has not bound to the antigen to be measured are separated from each other.

5. The chip according to claim 4, wherein a solid-phase antigen has been fixed to the reaction chamber, the antibody that has not bound to the antigen to be measured has bound to the solid-phase antigen, and by the wash, the antibody that has not bound to the antigen to be measured is left in the reaction chamber while the antigen-antibody complex moves into the effluent chamber.

6. The chip according to claim 4, wherein a solid-phase antibody has been fixed to the reaction chamber, the antigen-antibody complex is a conjugate of the solid-phase antibody, the antigen to be measured and the antibody, and by the wash, the antigen-antibody complex is left in the reaction chamber while the antibody that has not bound to the antigen to be measured moves into the effluent chamber.

* * * * *